United States Patent [19]

Larsson et al.

[11] Patent Number: 4,971,833

[45] Date of Patent: Nov. 20, 1990

[54] METHOD OF COATING SOLID PARTICLES WITH A HYDROPHILIC GEL

[75] Inventors: Per-Olof Larsson; Kersti B. Johnson; Ulf T. G. Nylen; Per I. O. Wikstrom; Ingrid K. Zetterstrand, all of Lund, Sweden

[73] Assignee: Excorim KB, Sweden

[21] Appl. No.: 116,020

[22] Filed: Nov. 2, 1987

[30] Foreign Application Priority Data

Nov. 3, 1986 [SE] Sweden .................. 8604684

[51] Int. Cl.$^5$ .................. B01J 13/04; B01D 15/08; G01N 30/48

[52] U.S. Cl. .................. 427/213.33; 427/213.3; 210/635; 210/656; 502/403; 502/439; 435/177

[58] Field of Search ........... 427/213.3, 213.31, 213.33, 427/213.36, 213.35, 213.32; 210/653, 656, 502.1; 502/402, 405, 407, 403, 439; 428/402.24

[56] References Cited

U.S. PATENT DOCUMENTS

| | | | |
|---|---|---|---|
| 3,436,355 | 4/1969 | Bakan | 427/213.33 |
| 3,594,327 | 7/1971 | Becsay | 427/213.33 X |
| 3,640,809 | 2/1972 | Polson et al. | 210/656 X |
| 3,816,331 | 6/1974 | Brown, Jr. et al. | 427/213.3 |
| 4,143,201 | 3/1979 | Miyashiro et al. | 210/635 X |
| 4,335,017 | 6/1982 | Miles et al. | 210/656 X |
| 4,336,161 | 6/1982 | Rosevear et al. | 502/7 |
| 4,352,883 | 10/1982 | Lim | 435/182 X |
| 4,433,054 | 2/1984 | Chibata et al. | 435/182 X |
| 4,442,051 | 4/1984 | Rowe et al. | 428/402.24 X |
| 4,443,339 | 4/1984 | Rosevear | 210/635 |
| 4,518,693 | 5/1985 | Kuu | 435/182 X |
| 4,622,244 | 11/1986 | Lapka | 427/213.36 X |
| 4,673,734 | 6/1987 | Tayot et al. | 435/176 X |
| 4,732,811 | 3/1988 | Margel | 428/402.24 X |

FOREIGN PATENT DOCUMENTS

| | | |
|---|---|---|
| 0048110 | 3/1982 | European Pat. Off. |
| 0266580 | 5/1988 | European Pat. Off. |
| 1223589 | 12/1968 | United Kingdom |
| 2133308 | 7/1984 | United Kingdom |

OTHER PUBLICATIONS

"Agarose Gels in HPLC Separation of Biopolymers," S. Hjerten, *Trends in Analytical Chemistry*, vol. 3, No. 3, Mar. 1984, pp. 87–90.

*Primary Examiner*—Richard D. Lovering
*Assistant Examiner*—John M. Covert
*Attorney, Agent, or Firm*—Lerner, David, Littenberg, Krumholz & Mentlik

[57] ABSTRACT

Methods for coating hydrophilic gels onto the surface of solid particles are disclosed which include utilizing hydrophilic solid particles, intimately admixing these hydrophilic solid particles with a hydrophilic gel-forming substance at a temperature above the gelling temperature so as to coat the solid hydrophilic particles, and then separating these coated particles from each other and cooling them to a temperature below the gelling temperature. The use of these coated particles is also disclosed in connection with various separation processes, such as an ion exchanger, in those cases where the gel-forming substance contains charged groups, or providing the particles with suitable adsorbent groups.

18 Claims, No Drawings

METHOD OF COATING SOLID PARTICLES WITH A HYDROPHILIC GEL

FIELD OF THE INVENTION

The present invention is directed to methods for coating hydrophilic gels onto the surface of solid particles. More particularly, the present invention is directed to solid particles coated with a layer of hydrophilic gel, particularly for use in chromatography. Still more particularly, the present invention is directed to solid particles coated with hydrophilic gels used as supports for different adsorbent groups.

BACKGROUND OF THE INVENTION

There exists a substantial need for various particles which are suitable for use as supports for different adsorbent groups in the field of chemistry, in general in connection with chromatography, and in particular in connection with immuno-absorption therapy. Such supports which have a large active surface and which can be rapidly and effectively brought into equilibrium with a flowing medium and also offer a low flow resistance thereto are especially desirable in this context. A support which presents such properties may consist of a solid inner core which has only small pores, or preferably none at all, which is coated with a thin layer of a gel which acts as a bonding medium for such adsorbent groups.

Columns which contain solid supports with immunoadsorbents immobilized thereon are found, for example, in U.S. Pat. Nos. 4,180,383 and 4,215,688. In at least the above-mentioned '383 patent, there is described a support which consists of an inner solid core with one or more outer layers of active material. However, the description of how these outer layers is produced is quite inadequate in this patent. It is therefore an object of the present invention to provide a method for the manufacture of such supports and more particularly to solid cores coated with hydrophilic gels.

SUMMARY OF THE INVENTION

In accordance with the present invention, these and other objects have now been realized by applicants' invention of a method for coating a hydrophilic gel onto the surface of a solid particle which includes providing hydrophilic solid particles, intimately admixing these hydrophilic solid particles with a precursor for the hydrophilic gel at an admixing temperature which is greater than the temperature at which the gel is formed in order to coat each of the hydrophilic solid particles with a layer of that precursor, separating the coated hydrophilic solid particles from each other, and lowering the admixing temperature to the predetermined gelling temperature for that gel in order to produce a layer of hydrophilic gel on the hydrophilic solid particles. In accordance with a preferred embodiment, the separating of the coated hydrophilic solid particles from each other comprises dispersing these particles in a hydrophobic solvent. Preferably, the lowering of the admixing temperature comprises cooling the hydrophobic solvent, and in a highly preferred embodiment, a dispersing agent is added to the hydrophobic solvent in order to assist in the dispersion step.

In accordance with another embodiment of the method of the present invention, each of the hydrophilic solid particles, the precursor for the hydrophilic gel and the hydrophobic solvent has substantially the same density.

In accordance with another embodiment of the method of the present invention, the hydrophilic solid particles and/or the precursor for the hydrophilic gel have a density which is greater than the density of the hydrophobic solvent, and the hydrophobic solvent has an elevated viscosity so as to prevent the coated hydrophilic solid particles from contacting each other.

In accordance with another embodiment of the method of the present invention, intimate admixing of the hydrophilic solid particles with the precursor for the hydrophilic gel is carried out in the hydrophobic solvent.

In accordance with another embodiment of the method of the present invention, intimate admixing of the hydrophilic solid particles with the precursor for the hydrophilic gel is carried out prior to dispersing the coated hydrophilic solid particles in the hydrophobic solvent.

In accordance with another embodiment of the method of the present invention, separating of the coated hydrophilic solvent particles from each other includes a mechanical separation step. In a preferred embodiment, this step includes passing the coated hydrophilic solid particles through a screen having a plurality of openings of a size which permit only one of the coated hydrophilic solid particles to pass therethrough at a time. Preferably, the lowering of the admixing temperature in this embodiment comprises passing the coated hydrophilic solid particles into a cooling medium, which can be a cold gas, air, or a liquid solvent medium. In an embodiment in which the solvent medium is a hydrophobic solvent the method includes passing the coated hydrophilic solid particles through the hydrophobic solvent in a predetermined direction, and decreasing the temperature of the hydrophobic solvent along that predetermined direction so that the temperature of the hydrophobic solvent initially contacted by the coated hydrophilic solid particles is greater than the predetermined gelling temperature for the gel and the temperature of the hydrophobic solvent at a predetermined distance along the predetermined direction comprises the predetermined gelling temperature for the gel.

In accordance with the method of the present invention, it is therefore possible to coat solid particles with a hydrophilic gel by utilizing a method which is based at least in part on the generally known principle that hydrophilic substances and hydrophilic particles are drawn towards one another, while at the same time there is a negative or rejection effect existing with respect to hydrophobic substances. Utilization is made of this principle in the method of the present invention by selecting as the solid particles hydrophilic particles, which are then mixed with a gel-forming substance at a temperature above the gelling temperature of that substance so that the gel-forming substance is made to cover each individual particle, and whereupon the particles are thus separated from each other and cooled to a temperature below the gelling temperature. As can be seen from the present disclosure, mixing as well as separations may take place in a number of different ways.

As is thus set forth in a preferred embodiment of the present invention, the separation step takes place by dispersing the coated particles in a hydrophobic solvent which is subsequently cooled. This can be carried out, for example, with vigorous and effective stirring which initially separates particles which might have a tendency to cohere with each other, and then keeping these particles separate from each other. It has thus been found that the hydrophilic gel-forming substance is drawn toward the individual hydrophilic particles and deposits as a thin layer around these particles. Thus, on cooling the gel-forming substance naturally solidifies, whereafter the coated particles can be readily separated from the hydrophobic solvent.

The dispersion step is greatly facilitated by the use of an additional dispersing agent, such as a soap with a hydrophilic end and a hydrophobic end. Because of the nature of these structures, these agents automatically settle in the boundary layer between the hydrophilic gel and the hydrophobic solvent, again assisting in the dispersion step.

The dispersion step is further facilitated if the particles, the gel-forming substance and the hydrophobic solvent are selected so that they have substantially identical densities. It is also possible, however, to use particles and/or gel-forming substances which have a different density, preferably a higher density, than that of the hydrophobic solvent. In that case, however, it becomes necessary to select a hydrophobic solvent which has a high viscosity, so that the particles with the gel-forming substance coated thereon are prevented from rising or sinking too rapidly, and they are also prevented from making contact with one another, which can lead to clotting or adherence together.

It is preferable to mix the gel-forming substance with the solid particles separately before dispersion in the hydrophobic solvent. However, this can also be accomplished in the solvent itself.

As discussed above, the separation step can be carried out through the use of vigorous stirring of the coated particles in a solvent. As an alternative, however, the separation step can be effected by forcing the particles mixed with the gel-forming substance through a sieve or the like which has a mesh size such that only one coated particle at a time can pass through the respective holes therein. Such a sifting procedure also makes it clear that the coating on the individual particles becomes very even. Furthermore, in such a process from the sieve itself the separated particles can then be made to drop freely down into a cooling agent and/or solvent. The simplest and least expensive system that can be used in such a case is that of a cooling agent which consists of water which has a temperature below the gelling temperature. It has also been found, however, that a somewhat more uniform coating can be achieved if a hydrophobic solvent is instead utilized, in the same manner as set forth above. The surface temperature of this solvent can be made to exceed the gelling temperature, and at the same time the bottom temperature can be kept below that temperature. In this manner a uniform distribution of the gel-forming layer can be attained as the particles sink down to the region where the gel itself begins to solidify.

As the particular material for the solid particles a hydrophilic glass is preferably used. However, other materials can also be used, such as polyvinyl chloride (PVC), polyamide, polycarbonate, etc. In such a case, however, the particles generally need to be pretreated so as to first achieve a hydrophilic surface.

The particle size for the solid particles which is selected is preferably between about 0.001 and 5 mm, and most preferably between about 0.15 and 1 mm.

As a suitable gel material agarose may be utilized. For this material it has been found particularly appropriate to select a thickness for the gel layer of between about 0.0001 and 1.0 mm, and most preferably between about 0.001 and 0.004 mm. Alternatively, a gel can be used such as agar, cappa carrageenan, starch, and chitosan.

Subsequent to the gelling step, the coated particles can be separated from the cooling agent and/or solvent which has been utilized. The gel may then be washed and possibly strengthened, such as through cross-linking.

The gel-coated solid particles which are so obtained may either be used as such in various separating processes, for example as an ion exchanger, in the case where the gel-forming substance contains charged groups. As an alternative, the gel-coated particles may then be provided with suitable adsorbent groups, such as ion exchange groups, hydrophobic groups, or groups with biospecificity. Examples of such groups with biospecificity are enzyme inhibitors, enzymes, antibodies, and protein A from staphylococcus Aureus.

The present invention also relates to coated particles, which are manufactured in accordance with the method set forth above.

The present invention may be further understood with reference to the following working examples thereof.

EXAMPLE 1

Agarose covering of glass beads in paraffin oil

Materials utilized:
150 ml of paraffin oil;
1.2 grams of sorbitan sesquioleate;
6.0 grams of glass beads, having a diameter of approximately 0.2 mm; and
3.0 ml of 3% agarose, having a gelling temperature below about 30° C.

The procedure employed with these materials included heating of the paraffin oil with the above-identified sesquioleate to a temperature of between 40° and 45° C.

The agarose was then melted in the water, which was heated to the boiling point, and was then mixed with the glass beads at 45° C., whereupon the mixture was added to the oil, with stirring at about 750 rpm.

Stirring was continued at a temperature of between 40° and 45° C. for five minutes. Thereafter, the mixture was cooled for five minutes in ice water, with continued stirring, and this was continued for a further period of ten minutes, but now essentially at room temperature.

Finally, the coated glass beads were separated from the paraffin oil and washed on a coarse filter (0.1 mm) with small portions of ether and water.

The result obtained comprised glass beads coated with a gel layer having a thickness of between about 5 and 15μ.

EXAMPLE 2

Agarose covering of dextran (Sephadex ® G 25 coarse) in n-butanol

Materials utilized:
150 ml of n-butanol;
2 grams of Sephadex ® G 25, coarse; and
10 ml of 0.5 agarose, having a gelling temperature below about 30° C.

The procedure employed with these materials included heating of the n-butanol in a water bath to approximately 50° C. The dextran was then measured and allowed to swell in about 20 ml of distilled water. Excess water was removed by suction through a glass filter funnel. The agarose was then heated in the water until it had melted, and it was then mixed with the dextran at approximately 40° C. The mixture was then added to the n-butanol, and stirred for five minutes at 40° C.

The water bath was then removed, and the n-butanol was allowed to assume room temperature, while stirring was continued. Finally, the gel was washed on a glass filter funnel with 50% acetone and distilled water.

The result obtained comprised dextran particles coated with a gel layer having a thickness of between about 15 and 30μ.

EXAMPLE 3

Coating of agarose on glass beads of 0.5 mm diameter.

In this example, 0.5 mm glass beads were boiled under reflex with 5% $HNO_3$ for a period of 10 minutes, and then washed with distilled water. They were then dried overnight at a temperature of 170° C.

3% agarose (Sea Plaque ® from FMC Corp.) having a gelling temperature of below 30° C. was then placed in a heating chamber, at a temperature of 41° C.

40 ml of the glass beads and 4 ml of the agarose were then mixed in a 200 ml round-bottom flask with a ground-glass stopper. Everything had been preheated to 41° C. Mixing was then carried out for three minutes by shaking the flask vigorously by hand. The flask was then maintained at 41° C. with continued shaking for a period of 10 minutes, whereupon the shaking was stopped, and the glass beads were poured out onto a strainer with 0.8 mm holes. The strainer had also been heated to 41° C. The straining step was then also thus carried out at this temperature. The glass beads with the adsorbed agarose were then forced through the strainer, with the help of a brush. They were then allowed to fall down directly into a 5 liter beaker, which was half filled with ice-cold water.

The results obtained comprised glass beads covered by solidified agarose which collected at the bottom of the beaker. The gel layer had a thickness of between about 4 and 10μ, and a relatively even coating was obtained.

EXAMPLE 4

Cross-linkage of agarose-coated glass beads

Materials utilized:
6.0 grams of agarose-coated glass beads (0.2 mm in diameter);
6.0 ml of 1 molar NaOH;
30 mg of $NaBH_4$; and
0.6 ml of epichlorhydrin.

The procedure employed with these materials included washing the agarose-coated glass beads with distilled water, and then weighing out a quantity of 6.0 grams. This measured quantity was then suspended in a small amount of distilled water, and the NaOH with $NaBH_4$ were added, followed by the epichlorhydrin. The mixture was then contained in a tube, which was rocked very gently overnight, with one turn approximately every twenty minutes.

The gel was then washed with distilled water until all of the NaOH, and any epichlorhydrin which might remain therein, had been removed. Neutralization with acetic acid was then carried out.

The result obtained comprised a substantially strengthened gel layer.

EXAMPLE 5

Coating of agarose on polyamide particles

In this example, polyamide-6 particles, having a diameter of 0.5 mm, were washed with a detergent (Duponol R A ®) in an alkaline medium. The polyamide was subsequently weakly hydrolyzed with 3.65 molar HCL at an elevated temperature. The polyamide was then washed with distilled water and dried. 900 mg of agarose (Sea Kem ME ® from FMC Corp.) was then suspended in 30 ml of distilled water, and boiled under reflex for 10 minutes.

A mixture of 150 ml of toluene, 50 ml of carbon tetrachloride and 0.3 grams of sorbitan sesquiolate were then heated to 50° C.

40 ml polyamide granules were then added to the agarose. Alternatively, the polyamide granules could be poured into the organic solvent first, and the agarose then added to the suspension of polyamide in toluene-carbon tetrachloride.

The agarose with polyamide was then poured into the organic solvent and stirred at a stirring rate of 1500 rpm. This stirring was then allowed to continue for five minutes, whereafter the suspension was cooled with continued stirring. The cooling was performed by placing the beaker in an ice bath. When the solution had cooled down to room temperature the excess solution was filtered off through a glass filter.

The gel was finally washed on the glass filter with toluene, diethyl and water.

Upon microscopic examination of the gel it was evident that each polyamide particle had acquired a thin layer of agarose having a thickness of between about 15 and 30μ.

As can be seen from the above examples, where organic solvent and water are utilized it is preferable that they have a low mutual solubility, in which case they would tend to form two phases.

In the case where the various substances utilized in this operation have the same density, and a water soluble gel is utilized, the density of this gel-forming substance in the liquid state can be adjusted through the addition of a salt. Therefore, the density may be adjusted, for example, with the aid of potassium iodide in the range of from about 1.0 grams per $cm^3$ to 1.7 grams per $cm^3$ for the gelling water phase.

In order to adjust the density of the hydrophobic phase, mixtures, for example, of toluene and carbon tetrachloride can be used, in the range of from about 0.9 to 1.6 grams per $cm^3$. If even greater densities are required, bromoform can be utilized instead of carbon tetrachloride. Most plastic materials, including polyamides, polycarbonates, polystyrenes, PVC, acrylates, etc. have a density within the range of between about 1 gram per $cm^3$ to 1.6 grams per $cm^3$. Inorganic materials, such as glass or coal, for example, on the other hand, have considerably higher densities.

Many plastic materials are hydrophobic by their very nature. However, most plastics can be rendered hydrophilic, at least on their surface, by means of modification of that surface so that the surface layer becomes hydrophilic. Such modification can be carried out in a number of different ways. Most often, however, the material is subjected to strong acids, oxidizing agents, radiation, or strong bases in an initial step. This achievement is sometimes sufficient to render the surface hydrophilic. In other cases, however, simultaneous with this aggressive treatment, some substance may be present which helps bond to the surface and render it hydrophilic.

The gel layer can be alternatively strengthened by chemical cross-linkages which can be obtained by bonding together bifunctional reagents with the matrix. The majority of hydrophilic gels contain free hydroxyl groups. Cross-linkage between free hydroxyl groups can be established, for example, by means of:

Epichlorhydrin:

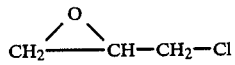

2-3 dibromopropanol: Br—ChH$_2$—CHBr—CH$_2$OH

Diphenyl sulphone: CH$_2$=CH—SO$_2$—CH=CH$_2$

An alternative method for providing such cross-linking would be to manufacture the gel in a procedure which itself contains a quantity of reactive groups. These reactive groups can be obtained, for example, by oxidizing the hydroxyl groups to aldehyde groups. A variation of this procedure is to utilize gel-forming substances which from the outset contain a number of active groups. An example of this is glyoxyl agarose which contains free aldehyde groups.

After the glyoxyl agarose containing free aldehyde groups has been made to solidify, the gel can then simply be cross-linked by the addition of a diamino compound H$_2$N—CH$_2$—R—CH$_2$—NH$_2$, wherein R is (CH$_2$)n and where n is a number from 0 to 10, whereafter the Schiff bases formed are reduced, for example, with sodium borohydride NaBH$_4$.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for coating a hydrophilic gel having a predetermined gelling temperature onto the surface of a solid particle comprising providing hydrophilic solid particles, intimately admixing said hydrophilic solid particles with a precursor for said hydrophilic gel at an admixing temperature greater than said predetermined gelling temperature so as to coat each of said hydrophilic solid particles with a layer of said precursor for said hydrophilic gel, separating said coated hydrophilic solid particles from each other by means of a mechanical separation step comprising passing said coated hydrophilic solid particles through a screen member having a plurality of openings of a size that only one of said coated hydrophilic solid particles can pass through each of said plurality of openings, and lowering said admixing temperature to said predetermined gelling temperature while maintaining said coated hydrophilic solid particle separated from each other so as to produce a layer of said hydrophilic gel on said hydrophilic solid particles.

2. The method of claim 1 wherein said lowering of said admixing temperature comprises passing said coated hydrophilic solid particles into a cooling medium.

3. The method of claim 2 wherein said cooling medium is selected from the group consisting of cold gas, cold air, and a cold liquid solvent medium.

4. The method of claim 3 wherein said cold liquid solvent medium comprises water.

5. The method of claim 3 wherein said cold liquid solvent medium comprises a hydrophobic solvent.

6. The method of claim 5 including passing said coated hydrophilic solid particles through said hydrophobic solvent in a predetermined direction, and decreasing the temperature of said hydrophobic solvent along said predetermined direction so that the temperature of said hydrophobic solvent initially contacted by said coated hydrophilic solid particles is greater than said predetermined gelling temperature and said temperature of said hydrophobic solvent at a predetermined distance along said predetermined direction comprises said predetermined gelling temperature.

7. The method of claim 1 wherein said hydrophilic solid particles comprise hydrophilic glass particles.

8. The method of claim 1 wherein said hydrophilic solid particles comprise hydrophobic particles selected from the group consisting of polyvinyl chloride, polyamide, polyacrylate, methylmethacrylate, polystyrene, polycarbonate, and mixtures thereof treated so as to produce a hydrophilic surface thereon.

9. The method of claim 1 wherein said hydrophilic solid particles have a particle size of between about 0.001 and 5 mm.

10. The method of claim 9 wherein said hydrophilic solid particles have a particle size of between about 0.15 and 1 mm.

11. The method of claim 1 wherein said hydrophilic gel is selected from the group consisting of agarose, agar, cappa carrageenan, starch, chitosan, and mixtures thereof.

12. The method of claim 11 wherein said hydrophilic gel comprises agarose.

13. The method of claim 12 wherein said coating of said hydrophilic gel on said hydrophilic solid particles has a thickness of between about 0.0001 and 1.0 mm.

14. The method of claim 13 wherein said coating has a thickness of between about 0.001 and 0.05 mm.

15. The method of claim 1 including washing said coated hydrophilic solid particles.

16. The method of claim 15 including cross-linking said gel layer.

17. The method of claim 1 including chemically bonding absorbent groups to said coating of said hydrophilic gel.

18. The method of claim 17 wherein said absorbent groups are selected from the group consisting of ion exchange groups, hydrophobic groups, enzyme inhibitors, enzymes, antigens, protein A, and antibodies.

* * * * *